US008618337B2

(12) United States Patent
Zarbakhsh et al.

(10) Patent No.: US 8,618,337 B2
(45) Date of Patent: Dec. 31, 2013

(54) PROCESS FOR PREPARING POLYETHER ALCOHOLS

(75) Inventors: Sirus Zarbakhsh, Central Hong Kong (CN); Markus Schuette, Osnabrueck (DE); Marc Fricke, Osnabrueck (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/092,467

(22) Filed: Apr. 22, 2011

(65) Prior Publication Data

US 2011/0263742 A1 Oct. 27, 2011

Related U.S. Application Data

(60) Provisional application No. 61/327,740, filed on Apr. 26, 2010.

(51) Int. Cl.
*C07C 43/00* (2006.01)
*C08G 18/00* (2006.01)

(52) U.S. Cl.
USPC ........... 568/608; 568/606; 568/607; 568/626; 568/648; 568/662; 568/78; 568/79; 521/137; 521/155; 521/156; 521/157; 521/158; 521/159; 521/160; 521/170; 521/172; 521/174

(58) Field of Classification Search
USPC ................. 568/606, 607, 608, 626, 648, 662; 521/137, 155, 156, 157, 158, 159, 160, 521/170, 172, 174; 528/78, 79
See application file for complete search history.

(56) References Cited

U.S. PATENT DOCUMENTS

| 4,209,609 | A | | 6/1980 | Haas | |
|---|---|---|---|---|---|
| 4,391,728 | A | * | 7/1983 | Korczak et al. | 252/182.25 |
| 4,562,290 | A | | 12/1985 | Korczak et al. | |
| 5,141,968 | A | * | 8/1992 | Dietrich et al. | 521/167 |
| 6,339,110 | B1 | * | 1/2002 | Cappella et al. | 521/131 |

FOREIGN PATENT DOCUMENTS

| DE | 2017 038 | | 10/1970 | | |
|---|---|---|---|---|---|
| DE | 37 40 634 | A1 | 6/1989 | | |
| DE | 42 32 970 | A1 | 4/1994 | | |
| EP | 0 318 784 | B1 | 6/1989 | | |
| WO | WO 9947581 | A1 | * | 9/1999 | C08G 65/26 |
| WO | WO 2005/044889 | A1 | 5/2005 | | |

OTHER PUBLICATIONS

Imidazole, a High Efficiency Alkoxylation Catalyst. Ionescu et al. Polyurethanes Conference 2000: Defining the Future Through Technology. pp. 311-322.*
U.S. Appl. No. 13/410,616, filed Mar. 2, 2012, Schuette, et al.
U.S. Appl. No. 13/590,353, filed Aug. 21, 2012, Emge, et al.
U.S. Appl. No. 13/813,300, filed Jan. 30, 2013, Loeffler, et al.

* cited by examiner

*Primary Examiner* — Michael L Leonard
(74) *Attorney, Agent, or Firm* — Oblon, Spivak, McClelland, Maier & Neustadt, L.L.P.

(57) ABSTRACT

The invention relates to a process for preparing polyether alcohols by reacting a) aromatic amines with b) alkylene oxides in the presence of c) a catalyst, wherein the alkylene oxide b) comprises at least 90% by weight, based on the weight of the component b), of propylene oxide and an amine is used as catalyst c).

10 Claims, No Drawings

PROCESS FOR PREPARING POLYETHER ALCOHOLS

DESCRIPTION

The invention relates to a process for preparing polyether alcohols by addition of alkylene oxides onto H-functional starter substances, in particular onto aromatic amines.

Polyether alcohols based on aromatic amines, in particular on methylenedianiline (MDA), which is usually present in admixture with its condensation products having more than two rings (p-MDA), and on tolylenediamine (TDA), and their use for preparing polyurethanes (PU), have been known for a long time. These products are used mainly for producing rigid polyurethane foams.

These products are usually prepared by reacting the aromatic amines with alkylene oxides, in particular ethylene oxide and/or propylene oxide, mostly in the presence of a catalyst.

U.S. Pat. No. 4,209,609 describes the preparation of TDA polyols in the hydroxyl number range 400-630 mg KOH/g, which are prepared by reacting TDA firstly with about 4 mol of ethylene oxide and subsequently with propylene oxide. These TDA polyols display some advantages (e.g. low coefficient of thermal conductivity). Further preparative methods are described in DE4232970A1 and U.S. Pat. No. 4,562,290. The amine-catalyzed preparation of TDA polyols, in which firstly 2-5 mol of ethylene oxide and then propylene oxide are added, is described in EP0318784B1 and DE3740634.

In the polyether alcohols described, ethylene oxide is always comprised in the polyether chain. This leads to a desired low viscosity of the polyether alcohols. On the other hand, the presence of ethylene oxide in the polyether chain leads to poorer compatibility with the blowing agents, in particular when hydrocarbons are used as blowing agents.

Pure propylene oxide polyethers in the abovementioned range of hydroxyl numbers are, as described, very highly viscous. The viscosity is frequently in the range of >55 000 mPas at 25° C. This is described, for example, in EP0318784 and in WO2005/044889. Polyether alcohols having such a high viscosity are disadvantageous for processing in PU systems. Firstly, high pressures are necessary to pump these polyols. This has a detrimental effect on the machines. Secondly, the polyols having high viscosities impair the flowability of the polyurethane system.

U.S. 4,391,728 describes the preparation of low-viscosity TDA polyols by means of KOH catalysis at temperatures above 140° C. Exclusively propylene oxide is used as alkylene oxide. The reaction requires at least 0.8% of alkali metal hydroxide as catalyst. As a result of the use of alkali metal hydroxides as catalysts, a complicated work-up, for example neutralization and subsequent filtration, is necessary, in particular as such high contents of catalyst.

DE 2017038 describes a process for preparing polyether alcohols based on ortho-TDA and propylene oxide, in which potassium hydroxide is used as catalyst. The polyether alcohols prepared by this process have very high viscosities. Thus, example 1 describes TDA-based polyether alcohols having a hydroxyl number of 435 mg KOH/g and a viscosity of 59 500 mPas at 25° C. In each case, only a small amount of alkylene oxide is added on at the beginning of the reaction in the absence of a catalyst (not more than 1.3 mol of alkylene oxide per mole of TDA). The viscosity can in principle be reduced by the use of high proportions of costarters, for example triethanolamine. However, such polyols cannot be used for all applications, in particular in the field of rigid polyurethane foams. As a result of, in particular, the relatively low functionality and the relatively low content of aromatic moieties in the polyether alcohol, many of the advantages associated with the use of polyether alcohols based on aromatic amines occur to only an excessively small extent, if at all.

It was an object of the present invention to develop polyether alcohols based on aromatic amines, in particular on TDA, in the preparation of which essentially exclusively propylene oxide is used as alkylene oxide and in which the disadvantages of the prior art do not occur. In particular, these polyether alcohols should have a low viscosity and a low content of unreacted aromatic amines used as starter compounds.

It has surprisingly been found that the use of amine catalysts gives polyols based on aromatic amines, in particular TDA, which have a low viscosity and comprise only propylene oxide as alkylene oxide.

The invention accordingly provides a process for preparing polyether alcohols by reacting a) aromatic amines with b) alkylene oxides in the presence of c) a catalyst, wherein the alkylene oxide b) comprises at least 90% by weight, based on the weight of the component b), of propylene oxide and an amine is used as catalyst c).

The invention also provides the polyether alcohols prepared by the process of the invention and also their use for preparing polyurethanes.

As aromatic amines a), it is in principle possible to use all known aromatic amines having at least one, preferably at least two and particularly preferably two amino group(s). The amino groups are usually primary amino groups.

In a preferred embodiment of the process of the invention, the aromatic amines are selected from the group consisting of aniline, TDA, MDA and p-MDA, particularly preferably from the group consisting of TDA and p-MDA. In particular, TDA is used.

When TDA is used, it is possible to use all isomers, either alone or in any mixtures with one another. In particular, it is possible to use 2,4-TDA, 2,6-TDA, mixtures of 2,4-TDA and 2,6-TDA, 2,3-TDA, 3,4-TDA, mixtures of 3,4-TDA and 2,3-TDA, and also mixtures of all isomers mentioned.

2,3-TDA and 3,4-TDA are frequently also referred to as ortho-TDA or vicinal TDA (vic-TDA). The two terms are used synonymously. The TDA can be exclusively vicinal TDA. In a particularly preferred embodiment of the process of the invention, the TDA comprises at least 90% by weight, particularly preferably at least 95% by weight and in particular at least 98% by weight, in each case based on the weight of the TDA, of vicinal TDA.

As alkylene oxide b), preference is given to using exclusively propylene oxide. For individual applications, it can be advantageous for a small amount of ethylene oxide to be additionally used. To avoid the abovementioned disadvantages, the proportion of ethylene oxide should not exceed 10% by weight. The content of ethylene oxide is, in this embodiment, preferably in the range from >0 to 10% by weight, particularly preferably from >0 to 5% by weight and in particular from >0 to 2% by weight, in each case based on the weight of the alkylene oxides b).

If ethylene oxide is used, it can be added on as a block or as a mixture with propylene oxide. When it is added on as a block, the addition reaction preferably occurs uncatalyzed at the beginning of the reaction. The addition of mixtures can also be carried out over the entire reaction.

As catalyst c), preference is given to using an amine. This can be a primary, secondary or tertiary amine. Furthermore, aliphatic or aromatic amines can be used. In the case of aliphatic amines, tertiary amines are particularly preferred. Amines also include amino alcohols. In an embodiment of the process of the invention, the amines can be aromatic heterocyclic compounds having at least one, preferably at least two nitrogen atom(s) in the ring.

The amines used as catalyst c) are preferably selected from the group consisting of trimethylamine, triethylamine, tripropylamine, tributylamine, N,N'-dimethylethanolamine, N,N'-dimethylcyclohexylamine, dimethylethylamine, dimethylbutylamine, N,N'-dimethylaniline, 4-dimethylaminopyridine, N,N'-dimethylbenzylamine, pyridine, imidazole, N-methylimidazole, 2-methylimidazole, 4-methylimidazole, 5-methylimidazole, 2-ethyl-4-methylimidazole, 2,4-dimethylimidazole, 1-hydroxypropylimidazole, 2,4,5-trimethylimidazole, 2-ethylimidazole, 2-ethyl-4-methylimidazole, N-phenylimidazole, 2-phenylimidazole, 4-phenylimidazole, guanidine, alkylated guanidines, 1,1,3,3-tetramethylguanidine, 7-methyl-1,5,7-triazabicyclo[4.4.0]dec-5-ene, 1,5-diazabicyclo[4.3.0]-non-5-ene, 1,5-diazabicyclo[5.4.0]undec-7-ene.

The amine catalysts c) can be used either alone or in any mixtures with one another.

In a preferred embodiment of the invention, the aliphatic amine c) is selected from the group consisting of N,N'-dimethylethanolamine, trimethylamine, triethylamine, dimethylethylamine, N,N'-dimethylcyclohexylamine.

In a preferred embodiment of the invention, the catalyst c) is N, N-dimethylethanolamine.

In a preferred embodiment of the invention, the catalyst c) is an imidazole, in particular imidazole.

The catalyst c) is preferably used in an amount of 0.1-1.0% by mass based on the sum of the weights of the components a), b) and c). This amount is particularly preferred when using aliphatic amines.

The heterocyclic amine catalysts c), in particular the imidazoles, are preferably used in an amount of from 0.01 to 0.5% by mass based on the sum of the weights of the components a), b) and c).

The catalyst c) can be added at the beginning of the reaction. The catalyst c) can be added before the addition of the alkylene oxides or, less preferably, simultaneously with the commencement of the introduction of the alkylene oxides.

In a particularly preferred embodiment of the invention, the addition reaction of the alkylene oxides can be carried out without a catalyst at the beginning and the catalyst can be added during the reaction. In this embodiment, the catalyst is preferably added after introduction of up to 3.4 mol of propylene oxide per mole of aromatic amine a), particularly preferably up to 3.0 mol of propylene oxide per mole of aromatic amine a).

The reaction of the amines with the alkylene oxide is carried out by customary methods described, for example, in EP 318 784. As described, the catalyst can be added before the reaction, simultaneously with the commencement of introduction of the alkylene oxides or during the reaction. Before introduction of the alkylene oxides, the starter mixture can be stripped, preferably at a pressure of 0.01-1 bar and a temperature of 25-150° C.

The aromatic amines a) used as starter substance can, in a preferred embodiment of the invention, be used as sole starter substance.

In a further embodiment of the invention, the aromatic amines can be used in combination with other compounds ai) having at least two hydrogen atoms which are reactive toward isocyanate groups. The compounds ai) are preferably alcohols or amino alcohols having a molecular weight of 40-400 g/mol, in particular 60-120 g/mol, and from 1 to 8, preferably 2 or 3, hydroxyl groups. The compounds ai) will hereinafter also be referred to as costarters.

The compound ai) is preferably selected from the group consisting of ethylene glycol, diethylene glycol, propylene glycol, dipropylene glycol, glycerol and triethanolamine and reaction products thereof with alkylene oxides.

In a further embodiment, ai) can be water.

The compounds ai) are preferably used in an amount of from 0.1 to 20% by weight, preferably from 0.1 to 10% by weight, in particular from 0.1 to 5% by weight, in each case based on the sum of the weights of the components a), b) and c).

The addition reaction of the alkylene oxides is preferably carried out at a temperature in the range from 90 to 150° C. and a pressure in the range from 0.1 to 8 bar. The introduction of the alkylene oxides is usually followed by an after-reaction phase to achieve ideally the complete conversion of the alkylene oxides. The crude polyether alcohol obtained in this way is freed of unreacted alkylene oxide and volatile compounds by distillation, preferably under reduced pressure.

The polyether alcohols prepared by the process of the invention preferably have a hydroxyl number in the range from 200 to 800 mg KOH/g, particularly preferably from 350 to 550 mg KOH/g and in particular from 350 to 470 mg KOH/g.

The polyether alcohols prepared by the process of the invention can be used for producing polyurethanes, in particular rigid polyurethane foams.

Owing to their low viscosity, the polyurethane systems produced using the polyether alcohols of the invention have good processability, in particular good flowability.

They are readily compatible with blowing agents, in particular blowing agents based on hydrocarbons, and have good storage stability. The compatibility with the isocyanate component is also increased, which leads to faster demolding.

The reaction of the TDA with the alkylene oxides is virtually quantitative, and virtually no free TDA is found in the polyether alcohols of the invention.

As indicated above, the polyether alcohols of the invention can be reacted with polyisocyanates to give rigid polyurethane foams.

As regards the starting materials used for this purpose, the following details may be provided:

Possible organic polyisocyanates are preferably aromatic polyfunctional isocyanates.

Specific examples are: tolylene 2,4- and 2,6-diisocyanate (TDI) and the corresponding isomer mixtures, diphenylmethane 4,4'-, 2,4'- and 2,2'-diisocyanate (MDI) and the corresponding isomer mixtures, mixtures of diphenylmethane 4,4'- and 2,4'-diisocyanates and, in the production of rigid polyurethane foams, in particular mixtures of diphenylmethane 4,4'-, 2,4'- and 2,2'-diisocyanates and polyphenylpolymethylene polyisocyanates (crude MDI).

The polyether alcohols of the invention are usually used in admixture with other compounds having at least two hydrogen atoms which are reactive toward isocyanate groups.

As compounds which have at least two hydrogen atoms which are reactive toward isocyanate and can be used together with the polyether alcohols used according to the invention, use is made of, in particular, polyether alcohols and/or polyester alcohols having OH numbers in the range from 100 to 1200 mg KOH/g.

The polyester alcohols used together with the polyether alcohols of the invention are usually prepared by condensation of polyfunctional alcohols, preferably diols, having from 2 to 12 carbon atoms, preferably from 2 to 6 carbon atoms, with polyfunctional carboxylic acids having from 2 to 12 carbon atoms, for example succinic acid, glutaric acid, adipic acid, suberic acid, azelaic acid, sebacic acid, decanedicarboxylic acid, maleic acid, fumaric acid and preferably phthalic acid, isophthalic acid, terephthalic acid and the isomeric naphthalenedicarboxylic acids.

The polyether alcohols used together with the polyether alcohols used according to the invention usually have a functionality of from 2 to 8, in particular from 3 to 8.

Particular preference is given to using polyether alcohols prepared by known processes, for example by anionic polymerization of alkylene oxides in the presence of catalysts, preferably amines and/or alkali metal hydroxides.

As alkylene oxides, use is usually made of ethylene oxide and/or propylene oxide, preferably pure 1,2-propylene oxide.

Starter molecules used are, in particular, compounds having at least 2, preferably from 4 to 8, hydroxyl groups or at least two primary amino groups in the molecule.

As starter molecules having at least 2, preferably from 3 to 8, hydroxyl groups in the molecule, preference is given to using trimethylolpropane, glycerol, pentaerythritol, castor oil, sugar compounds such as glucose, sorbitol, mannitol and sucrose, polyhydric phenols, resoles such as oligomeric condensation products of phenol and formaldehyde and Mannich condensates derived from phenols, formaldehyde and dialkanolamines and also melamine.

The polyether alcohols have a functionality of preferably from 2 to 8 and hydroxyl numbers of preferably from 100 mg KOH/g to 1200 mg KOH/g and in particular from 120 mg KOH/g to 570 mg KOH/g.

The use of difunctional polyols, for example polyethylene glycols and/or polypropylene glycols, having a molecular weight Mw in the range from 500 to 1500 g/mol in the polyol component enables the viscosity of the polyol component to be adapted.

The compounds having at least two hydrogen atoms which are reactive toward isocyanate also include chain extenders and crosslinkers which may be used concomitantly. The rigid polyurethane foams can be produced with or without the use of chain extenders and/or crosslinkers. The addition of bifunctional chain extenders, trifunctional and higher-functional crosslinkers or, if appropriate, mixtures thereof can prove to be advantageous for modifying the mechanical properties. Chain extenders and/or crosslinkers used are preferably alkanolamines and in particular diols and/or triols having molecular weights of less than 400 g/mol, preferably from 60 to 300 g/mol.

Chain extenders, crosslinkers or mixtures thereof are advantageously used in an amount of from 1 to 20% by weight, preferably from 2 to 5% by weight, based on the polyol component.

The polyurethane foams are usually produced in the presence of blowing agents. As blowing agent, preference is given to using water, which reacts with isocyanate groups to eliminate carbon dioxide. Physical blowing agents can also be used in combination with or in place of water. These are compounds which are inert toward the starting components and are usually liquid at room temperature and vaporize under the conditions of the urethane reaction. The boiling point of these compounds is preferably below 50° C. Physical blowing agents also include compounds which are gaseous at room temperature and are introduced under pressure into the starting components or dissolved therein, for example carbon dioxide, low-boiling alkanes and fluoroalkanes.

The physical blowing agents are usually selected from the group consisting of alkanes and cycloalkanes having at least 4 carbon atoms, dialkyl ethers, esters, ketones, acetals, fluoroalkanes having from 1 to 8 carbon atoms and tetraalkylsilanes having from 1 to 3 carbon atoms in the alkyl chain, in particular tetramethylsilane.

Examples which may be mentioned are propane, n-butane, isobutane and cyclobutane, n-pentane, isopentane and cyclopentane, cyclohexane, dimethyl ether, methyl ethyl ether, methyl butyl ether, methyl formate, acetone and also fluoroalkanes which can be degraded in the troposphere and therefore do not damage the ozone layer, e.g. trifluoromethane, difluoromethane, 1,1,1,3,3-pentafluorobutane, 1,1,1,3,3-pentafluoropropane, 1,1,1,2-tetrafluoroethane, difluoroethane and 1,1,1,2,3,3,3-heptafluoropropane, and also perfluoroalkanes such as $C_3F_8$, $C_4F_{10}$, $C_5F_{12}$, $C_6F_{14}$, and $C_7F_{16}$. Particular preference is given to pentanes, in particular cyclopentane. The physical blowing agents mentioned can be used either alone or in any combinations with one another.

The production of the polyurethanes can, if necessary, be carried out in the presence of catalysts, flame retardants and also customary auxiliaries and/or additives.

Further information regarding the starting compounds used may be found, for example, in Kunststoffhandbuch, volume 7 "Polyurethane", edited by Günter Oertel, Carl-Hanser-Verlag, Munich, 3rd edition, 1993.

The invention is illustrated by the following examples.

EXAMPLE 1

A 30 l pressure reactor provided with stirrer, jacket heating and cooling, metering facilities for solid and liquid substances and alkylene oxides and also facilities for blanketing with nitrogen and a vacuum system was heated to 80° C. and made inert a number of times. 6.2 kg of vicinal tolylenediamine was introduced into the reactor and the stirrer was started up at 150 revolutions per minute. The temperature was subsequently increased to 138° C. and 8.26 kg of propylene oxide (2.8 mol of propylene oxide/mole of vic-TDA) were metered in. After a reaction time of 2 hours, the temperature was reduced to 95° C. and 220 g of N,N'-dimethylethanolamine were added. The intermediate was reacted with a further 12.7 kg of propylene oxide at 95° C. The after-reaction proceeded for 2 hours at 95° C. The mixture was subsequently stripped under nitrogen for 20 minutes. This gave 26.1 kg of product having the following properties:
Hydroxyl number 390 mg KOH/g
Viscosity (25° C.) 33 500 mPas

EXAMPLE 2

51.02 g of vic-tolylenediamine were placed in a 300 ml pressure reactor. The stirrer was started and the temperature was increased to 138° C. 54.34 g of propylene oxide (2.24 mol of propylene oxide/mole of vic-TDA) were then metered in. After a reaction time of 2 hours, the temperature was reduced to 95° C. and 0.66 g of imidazole were added. A further 112.86 g of propylene oxide were then metered in. The after-reaction proceeded for 3 hours at 95° C. The mixture was subsequently evacuated under reduced pressure for 90 minutes. This gave 210 g of product having the following properties:
Hydroxyl number 405 mg KOH/g
Viscosity (25° C.) 17 469 mPas

EXAMPLE 3

51.00 g of vic-tolylenediamine were placed in the reactor used in example 2. The stirrer was started and the temperature was increased to 138° C. 54.34 g of propylene oxide (2.24 mol of propylene oxide/mole of vic-TDA) were then metered in. After a reaction time of 2 hours, the temperature was reduced to 95° C. and 0.22 g of imidazole were added. A further 112.86 g of propylene oxide were then metered in. The after-reaction proceeded for 3 hours at 95° C. The mixture was subsequently evacuated under reduced pressure for 90 minutes. This gave 206 g of product having the following properties:
Hydroxyl number 406 mg KOH/g
Viscosity (25° C.) 30 924 mPas

EXAMPLE 4

51.00 g of vic-tolylenediamine were placed in the reactor used in example 2. The stirrer was started and the temperature was increased to 138° C. 61.14 g of propylene oxide (2.52 mol of propylene oxide/mole of vic-TDA) were then metered in. After a reaction time of 2 hours, the temperature was reduced to 95° C. and 0.66 g of imidazole were added. A further 106.06 g of propylene oxide were then metered in. The after-reaction proceeded for 3 hours at 95° C. The mixture was subsequently evacuated under reduced pressure for 90 minutes. This gave 208 g of product having the following properties:
Hydroxyl number 412 mg KOH/g
Viscosity (25° C.) 24 650 mPas

EXAMPLE 5

51.00 g of vic-tolylenediamine were placed in the reactor used in example 2. The stirrer was started and the temperature was increased to 138° C. 53.98 g of propylene oxide (2.24 mol of propylene oxide/mole of vic-TDA) were then metered in. After a reaction time of 2 hours, the temperature was reduced to 95° C. and 1.81 g of N,N'-dimethylethanolamine were added. A further 112.76 g of propylene oxide were then metered in. The after-reaction proceeded for 3 hours at 95° C. The mixture was subsequently evacuated under reduced pressure for 90 minutes. This gave 202 g of product having the following properties:
Hydroxyl number 414 mg KOH/g
Viscosity (25° C.) 15 147 mPas

EXAMPLE 6 (comparison)

The reactor described in example 1 was heated to 80° C. and made inert a number of times. 5.65 kg of vic-tolylenediamine were introduced into the reactor and the stirrer was started. The temperature was subsequently increased to 138° C. and 7.50 kg of propylene oxide (2.8 mol of propylene oxide/mole of vic-TDA) were metered in. After a reaction time of 2 hours, the temperature was reduced to 100° C. and 91 g of 48% strength aqueous KOH were added. The temperature was increased to 138° C. and the intermediate was reacted with a further 11.74 kg of propylene oxide. The after-reaction proceeded for 2 hours at 138° C. The mixture was stripped with nitrogen for 20 minutes. 2.5% of water were subsequently added and the mixture was neutralized with phosphoric acid. The water was stripped out under reduced pressure and the product was filtered at 80° C. This gave 24.6 kg of product having the following properties:
Hydroxyl number 371 mg KOH/g
Viscosity (25° C., 5 1/s) 42 359 mPas

EXAMPLE 7 (comparison)

55.91 g of vic-tolylenediamine were placed in the reactor used in example 2. The stirrer was started and the temperature was increased to 138° C. 64.84 g of propylene oxide (2.44 mol per mole of vic-TDA) were then metered in. After a reaction time of 2 hours, the temperature was reduced to 95° C. and 1.39 g of aqueous potassium hydroxide (50%) were added. The temperature was increased to 138° C. again and a further 97.86 g of propylene oxide were metered in. The after-reaction proceeded for 3 hours at 138° C. The mixture was subsequently evacuated under reduced pressure for 90 minutes. This gave 211 g of product having the following properties:
Hydroxyl number 424 mg KOH/g
Viscosity (25° C., 5 1/s) 82 345 mPas Viscosity Determination:

The viscosity of the polyols was, unless indicated otherwise, determined at 25° C. in accordance with DIN EN ISO 3219 by means of a Rheotec RC 20 rotational viscometer using the spindle CC 25 DIN (spindle diameter: 12.5 mm; internal diameter of measuring cylinder: 13.56 mm) at a shear rate of 50 1/s.

Measurement of the Hydroxyl Number

The hydroxyl numbers were determined in accordance with DIN 53240.

The invention claimed is:

1. A process for preparing polyether alcohols by reacting a) aromatic amines comprising tolylenediamine with b) alkylene oxides in the presence of c) 0.01 to 0.5% by mass of a catalyst comprising imidazole, wherein the alkylene oxide b) comprises at least 90% by weight, based on the weight of the component b), of propylene oxide,
   wherein said aromatic amines and said alkylene oxides are reacted at a temperature of from 90 to 150° C.

2. The process according to claim 1 wherein the amine a) further comprises at least one amine selected from the group consisting of aniline, methylenedianiline and mixtures of methylenedianiline with condensation products thereof having more than two rings (p-MDA).

3. The process according to claim 1, wherein the amine a) comprises tolylenediamine having a content of at least 90% by weight of vicinal tolylenediamine, based on the total amount of tolylenediamine.

4. The process according to claim 1, further comprising reacting with said alkylene oxides, in addition to the amines a), a further compound ai) having at least two hydrogen atoms which are reactive toward isocyanate groups.

5. The process according to claim 1, wherein the alkylene oxide b) comprises exclusively propylene oxide.

6. A polyether alcohol prepared according to any one of claims 1 to 2 and 3 to 5.

7. A method for preparing polyurethanes comprising reacting a polyether alcohol according to claim 6 with a polyisocyanate.

8. The process according to claim 1, wherein said aromatic amines and said alkylene oxides are reacted is carried at a pressure of 0.1 to 8 bar.

9. The process according to claim 1, wherein a content of ethylene oxide is from >0 to 5% by weight based on alkylene oxides.

10. The process according to claim 1, wherein a content of ethylene oxide is from >0 to 2% by weight based on alkylene oxides.

* * * * *